United States Patent
Rubin et al.

(10) Patent No.: US 10,286,126 B2
(45) Date of Patent: May 14, 2019

(54) ADJUSTABLE LIPOSUCTION CANNULA

(71) Applicants: University of Pittsburgh—Of the Commonwealth System of Higher Education, Pittsburgh, PA (US); J. Peter Rubin, Pittsburgh, PA (US); Arielle A. Richter, Flagstaff, AZ (US); Aaron T. Ledgerwood, Pittsburgh, PA (US); Jessica C. Huynh, Pittsburgh, PA (US); Mark J. Gartner, Pittsburgh, PA (US); Kacey G. Marra, Canonsburg, PA (US); Stephen Holland, Willoughby, OH (US)

(72) Inventors: J. Peter Rubin, Pittsburgh, PA (US); Arielle A. Richter, Flagstaff, AZ (US); Aaron T. Ledgerwood, Pittsburgh, PA (US); Jessica C. Huynh, Philadelphia, PA (US); Kacey G. Marra, Canonsburg, PA (US); Stephen Holland, Willoughby, OH (US); Mark J. Gartner, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 681 days.

(21) Appl. No.: 14/440,562

(22) PCT Filed: Nov. 6, 2013

(86) PCT No.: PCT/US2013/068762
§ 371 (c)(1),
(2) Date: May 4, 2015

(87) PCT Pub. No.: WO2014/074606
PCT Pub. Date: May 15, 2014

(65) Prior Publication Data
US 2015/0297810 A1 Oct. 22, 2015

Related U.S. Application Data

(60) Provisional application No. 61/723,235, filed on Nov. 6, 2012.

(51) Int. Cl.
*A61B 17/34* (2006.01)
*A61M 1/00* (2006.01)

(52) U.S. Cl.
CPC ....... *A61M 1/0082* (2014.02); *A61B 17/3431* (2013.01); *A61M 1/008* (2013.01); *A61M 2202/08* (2013.01)

(58) Field of Classification Search
CPC ............... A61M 1/008; A61M 1/0082; A61M 2202/08; A61B 17/32002; A61B 17/3431
See application file for complete search history.

(56) References Cited

U.S. PATENT DOCUMENTS

| | | |
|---|---|---|
| 4,735,605 A | 4/1988 | Swartz |
| 5,665,101 A | 9/1997 | Becker et al. |
| (Continued) | | |

OTHER PUBLICATIONS

Coleman, et al. "Fat Grafting to the Breast Revisited: Safety and Efficacy." *American Society of Plastic Surgery* 119.3 (2007): 775-85.

(Continued)

*Primary Examiner* — Benjamin J Klein
(74) *Attorney, Agent, or Firm* — Klarquist Sparkman, LLP

(57) ABSTRACT

A device for removing fat from a body can include a pair of nested hollow members that each has at least one opening and an adjustment means for adjusting the orientation of the nested hollow members from a first configuration to a (Continued)

second configuration to change an amount of overlap between openings in the nested hollow members. The nested members can be deformable to change the shape of the openings.

21 Claims, 12 Drawing Sheets

(56) References Cited

U.S. PATENT DOCUMENTS

| | | | |
|---|---|---|---|
| 5,669,921 A * | 9/1997 | Berman | A61B 17/32002 |
| | | | 606/167 |
| 5,817,505 A | 10/1998 | Thompson et al. | |
| 6,676,677 B2 | 1/2004 | Klein | |
| 6,692,473 B2 | 2/2004 | St. Cyr et al. | |
| 7,828,775 B2 | 11/2010 | Okoniewski | |
| 2002/0151874 A1* | 10/2002 | Kolster | A61B 17/32002 |
| | | | 604/542 |
| 2008/0183201 A1 | 7/2008 | Berberich | |
| 2009/0076486 A1 | 3/2009 | Cucin | |
| 2012/0136277 A1* | 5/2012 | Landrigan | A61B 10/025 |
| | | | 600/566 |

OTHER PUBLICATIONS

Fodor, et al. "Suction-Assisted Lipoplasty: Physics, Optimization, and Clinical Verification." *Aesthetic Surgery Journal* 25.23 (2005): 234-46.

* cited by examiner

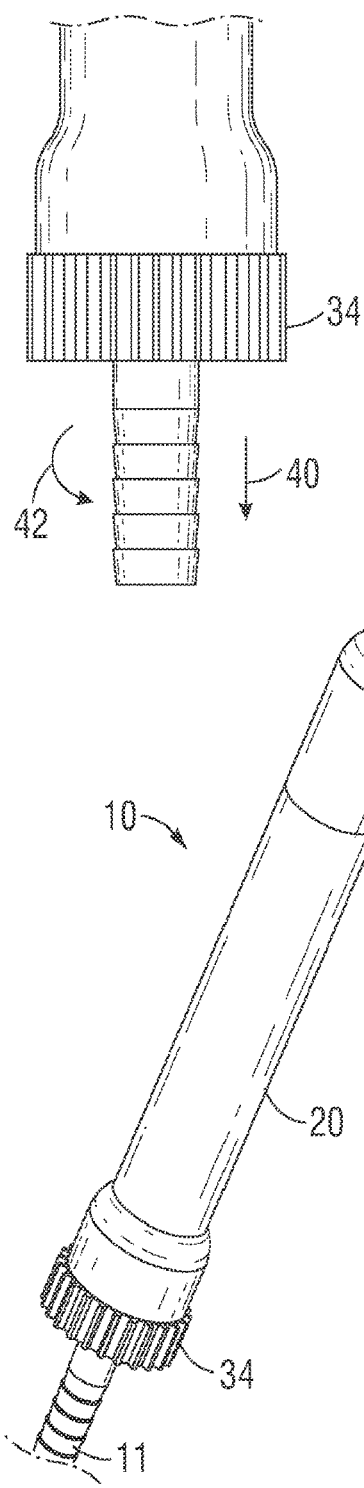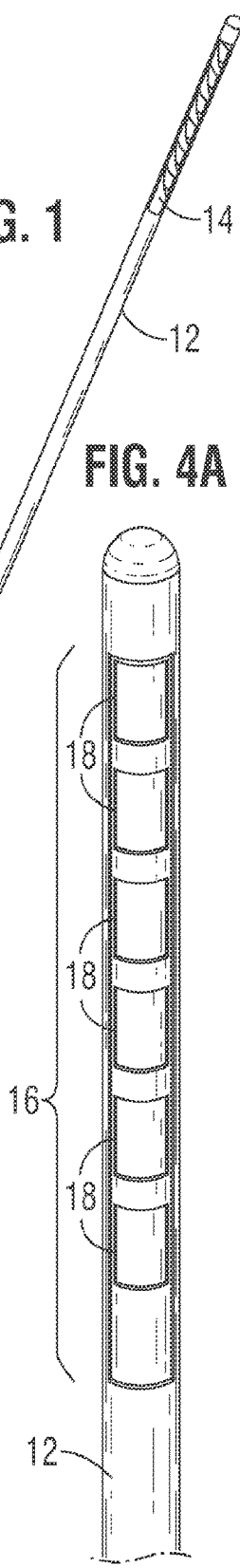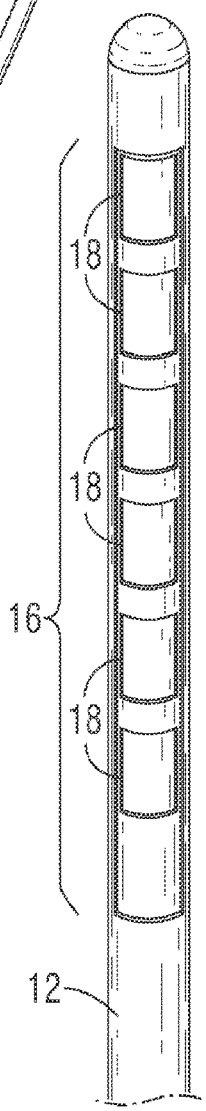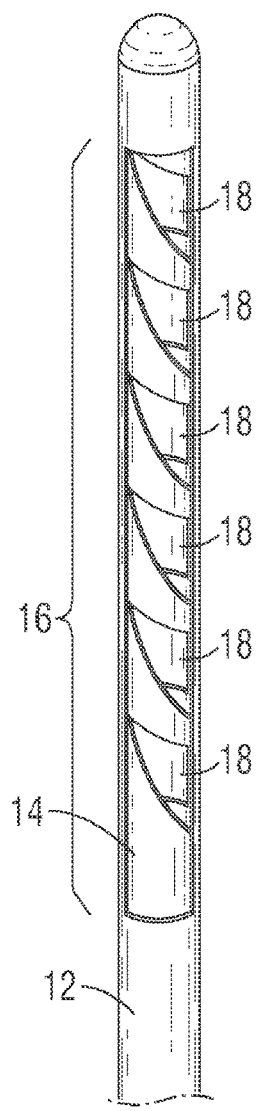

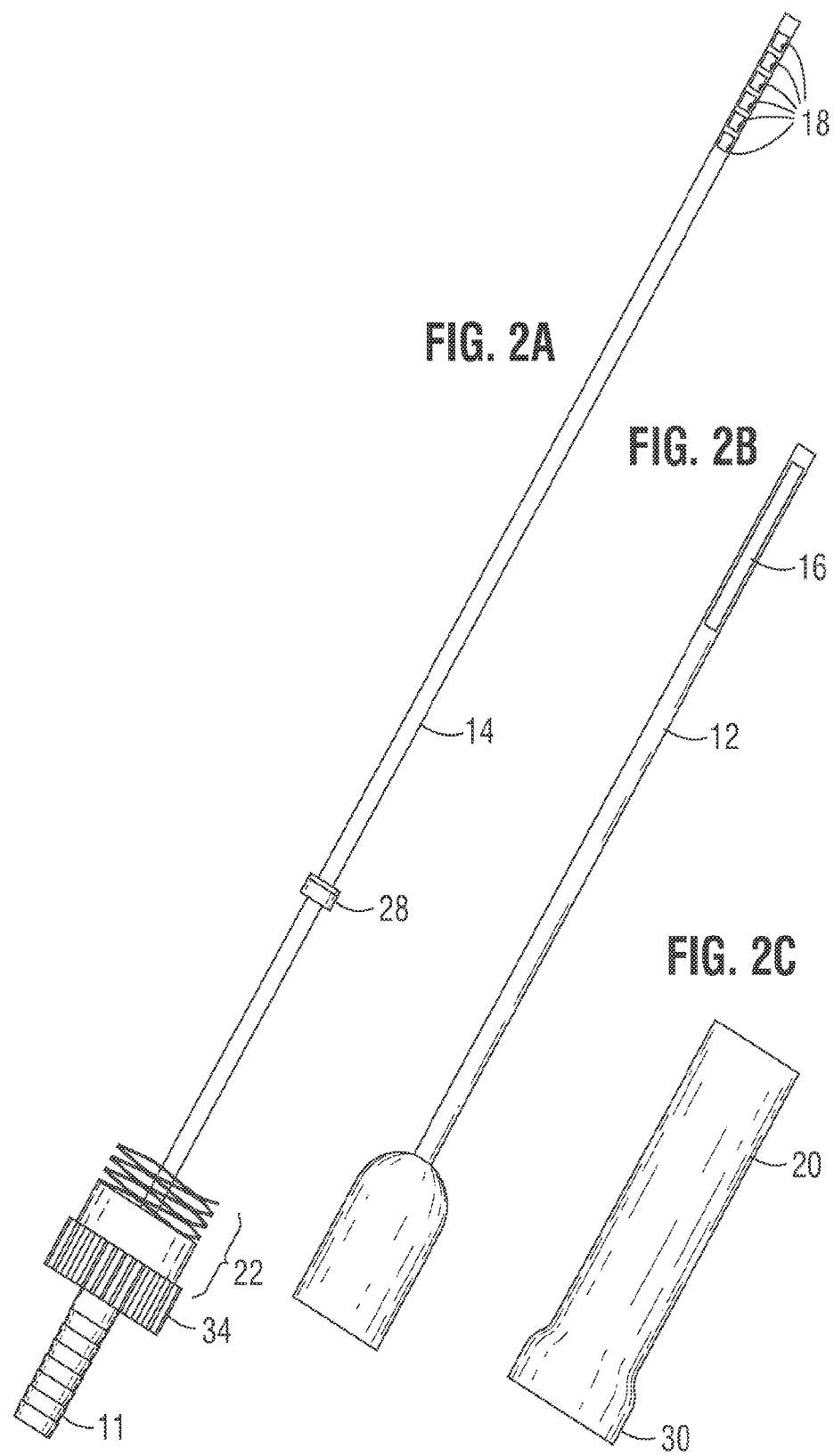

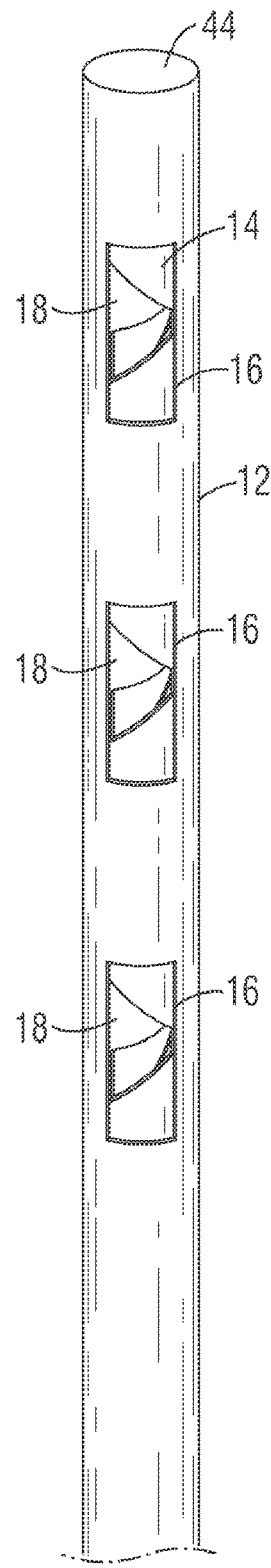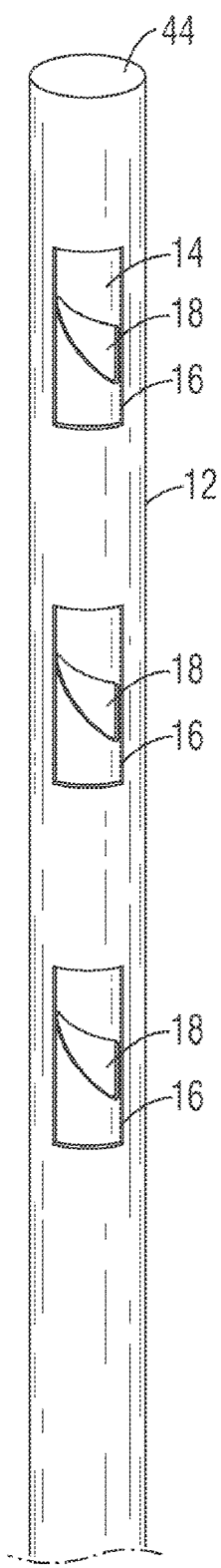

FIG. 8
FIG. 9
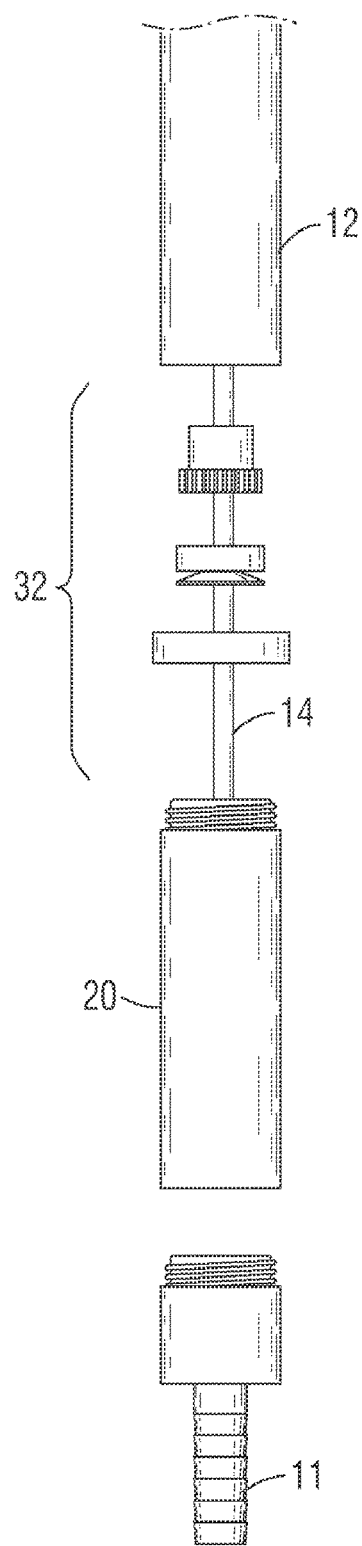
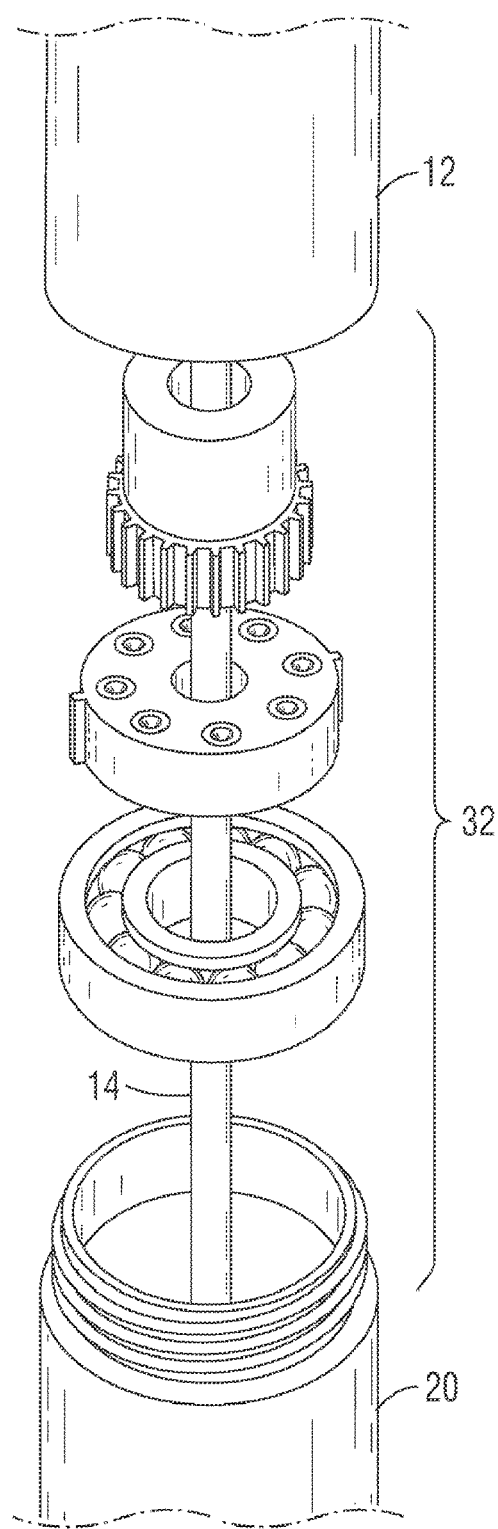

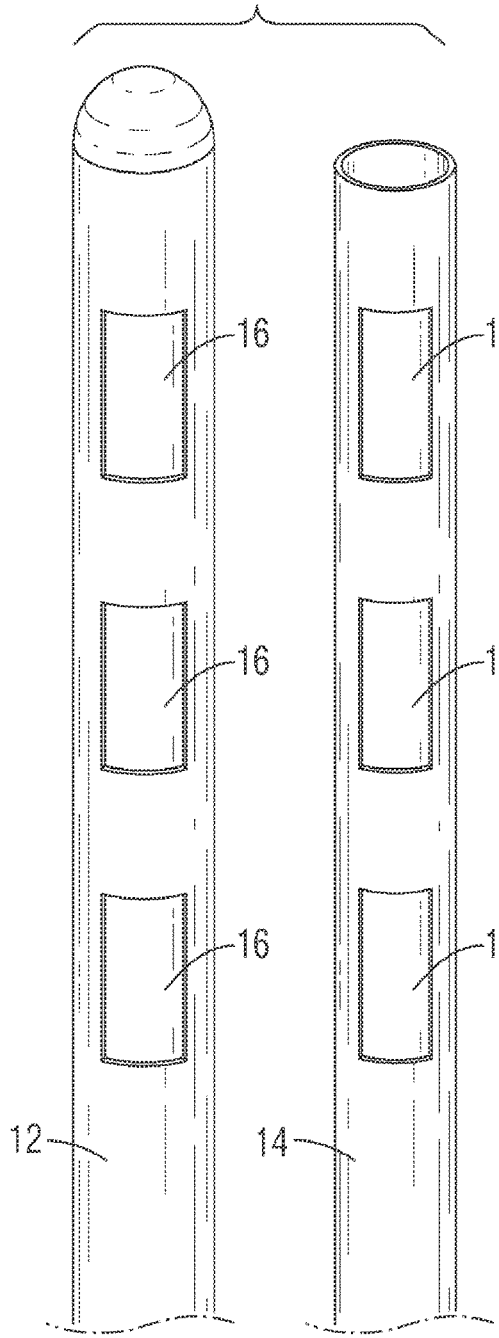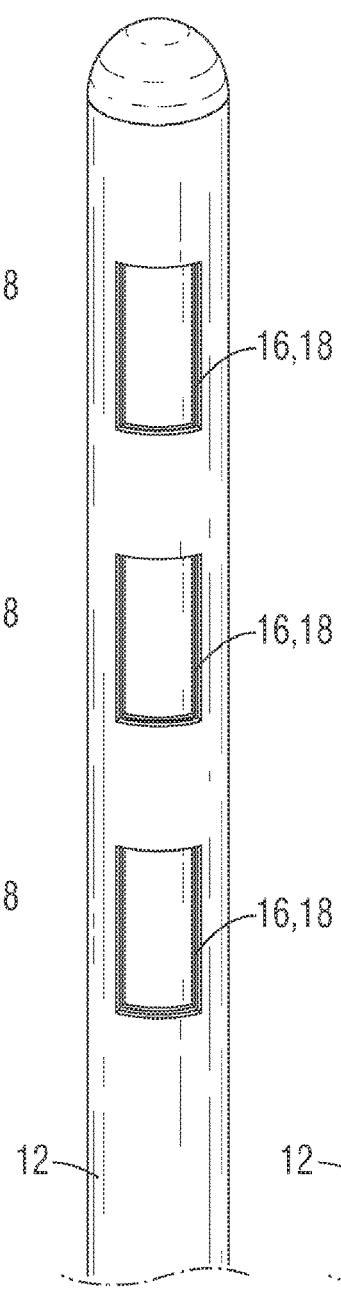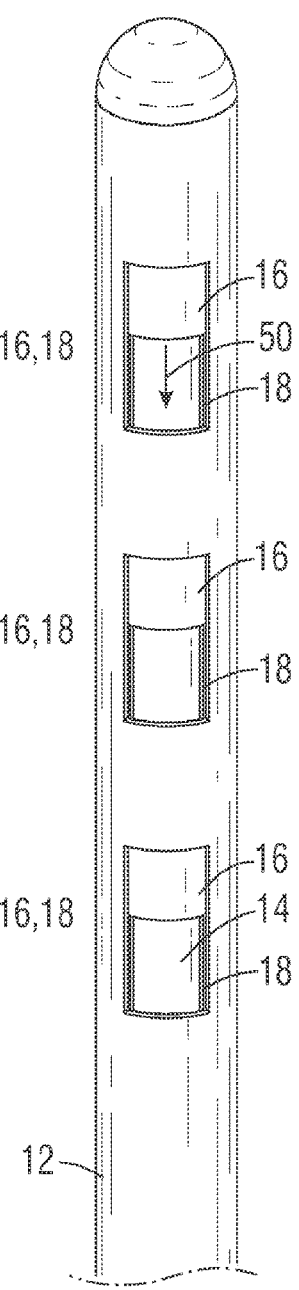

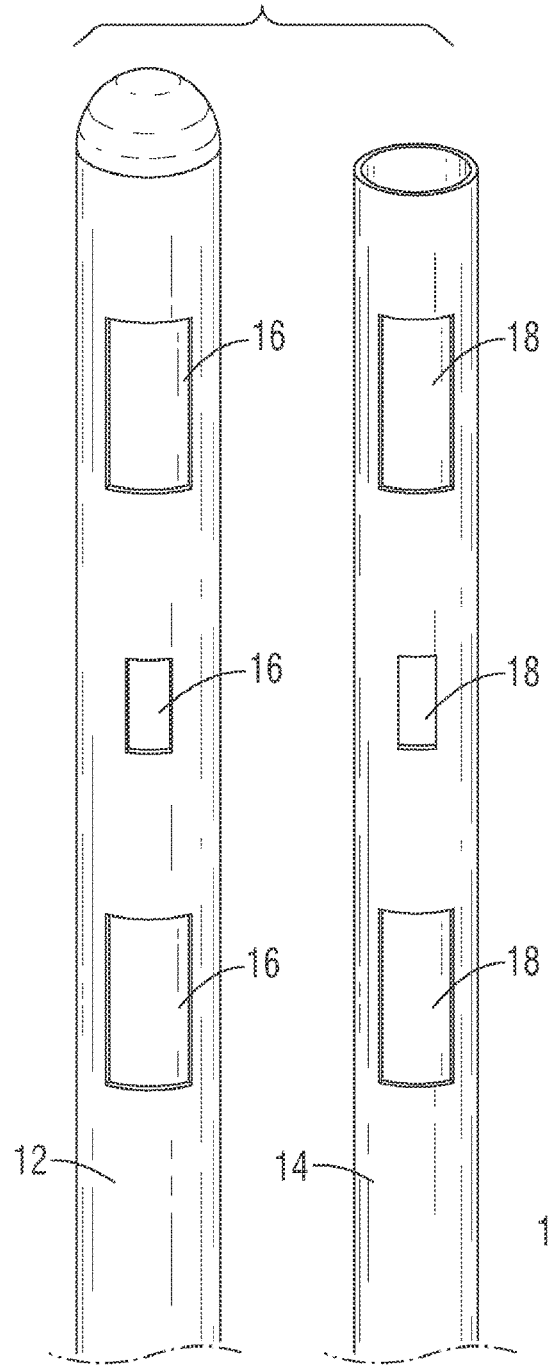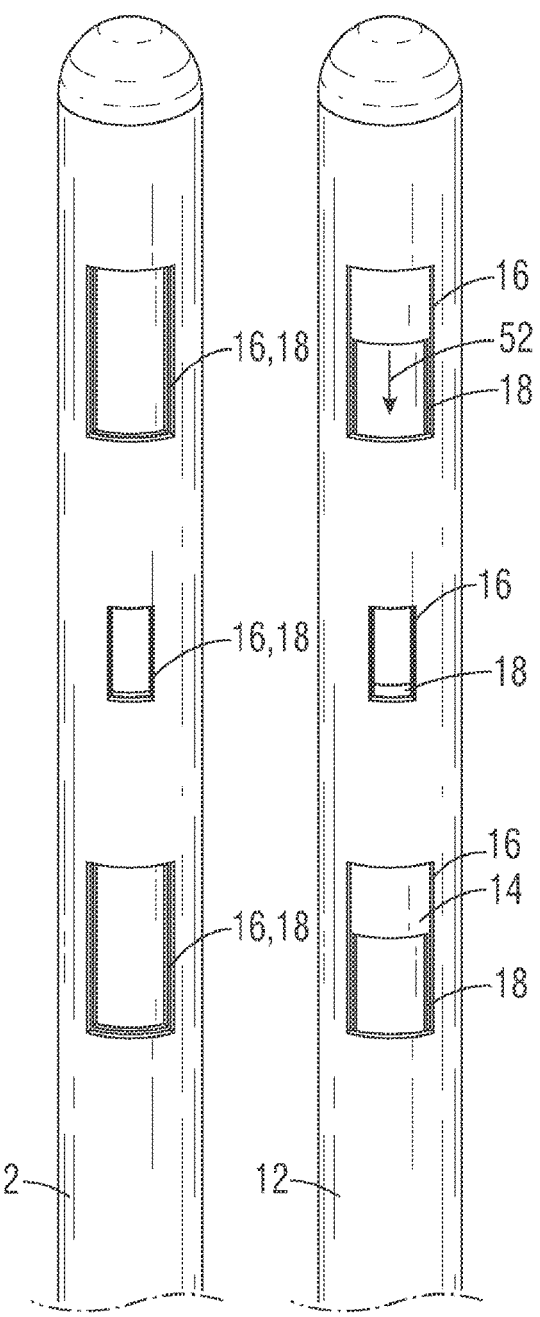

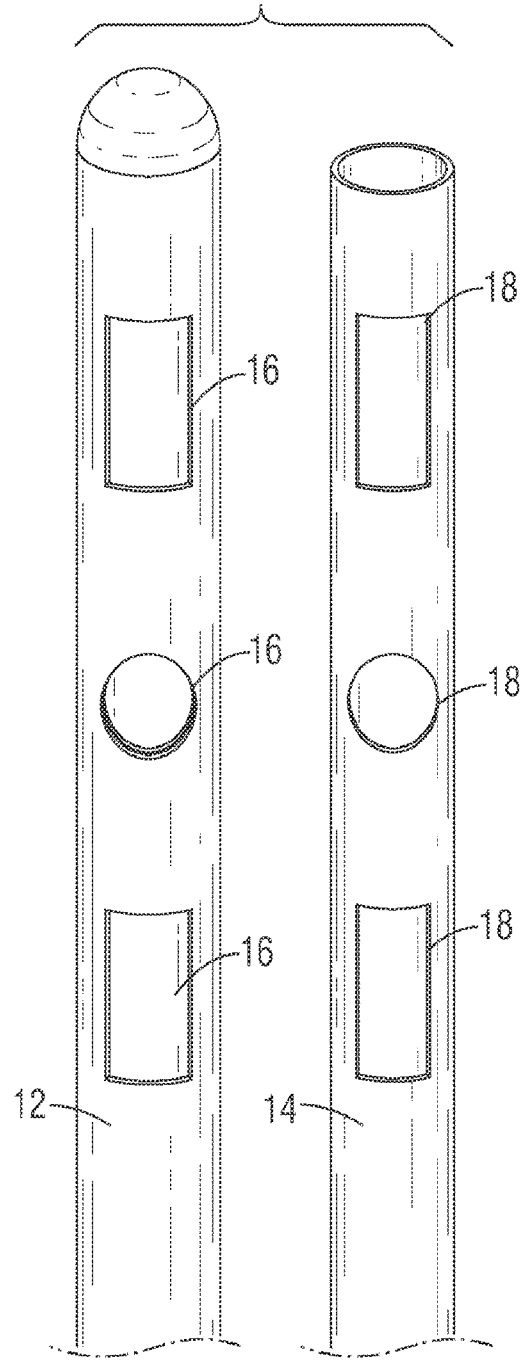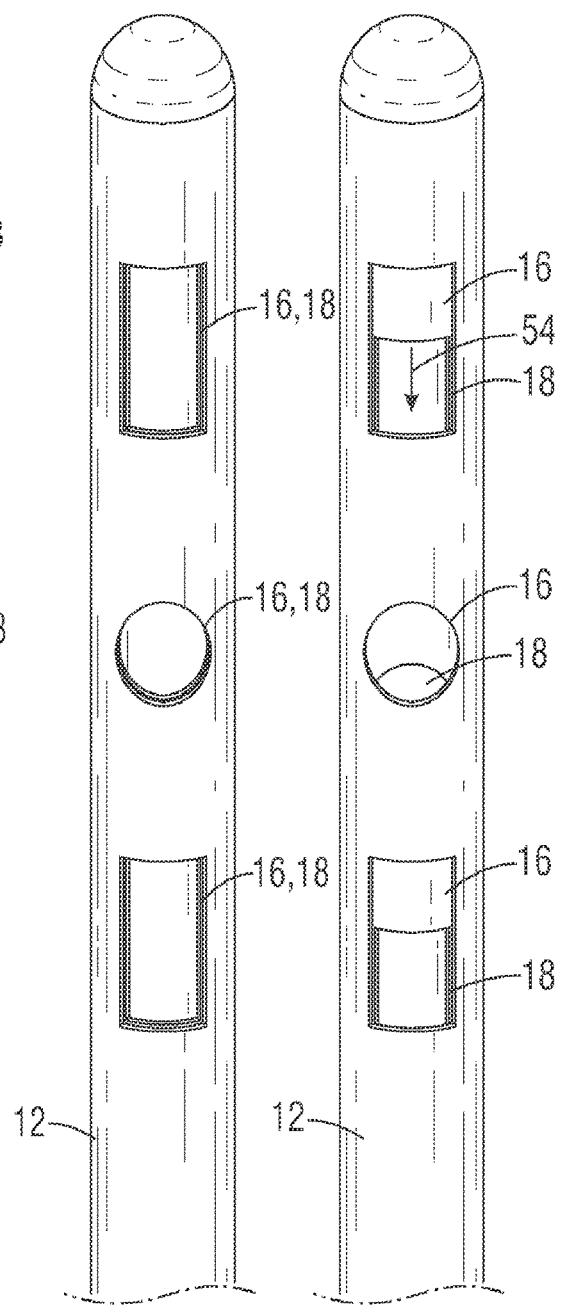

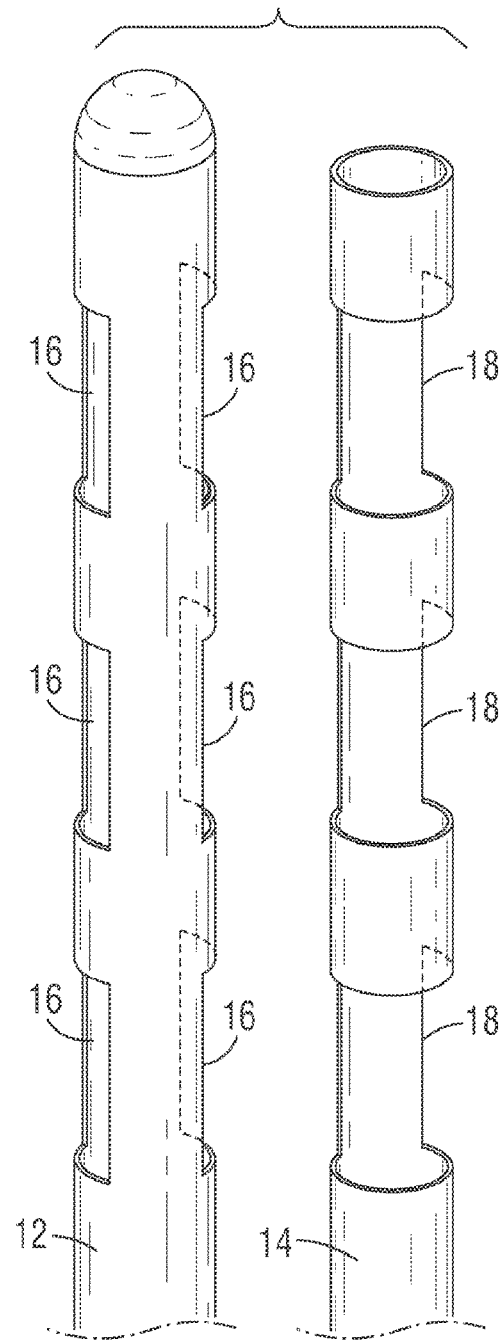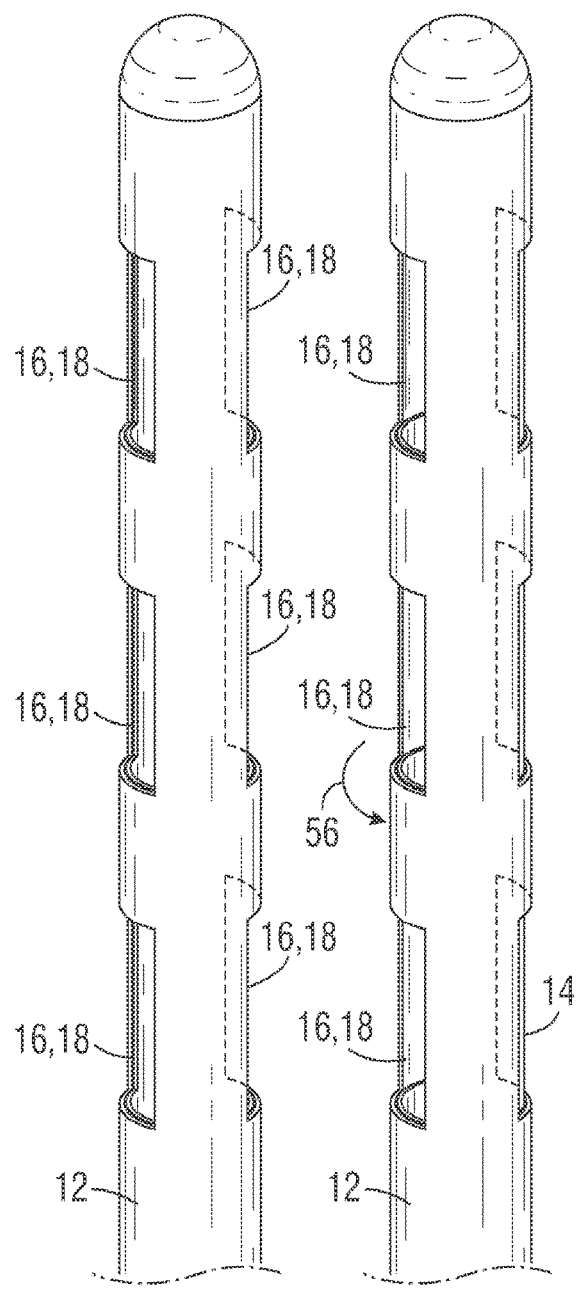

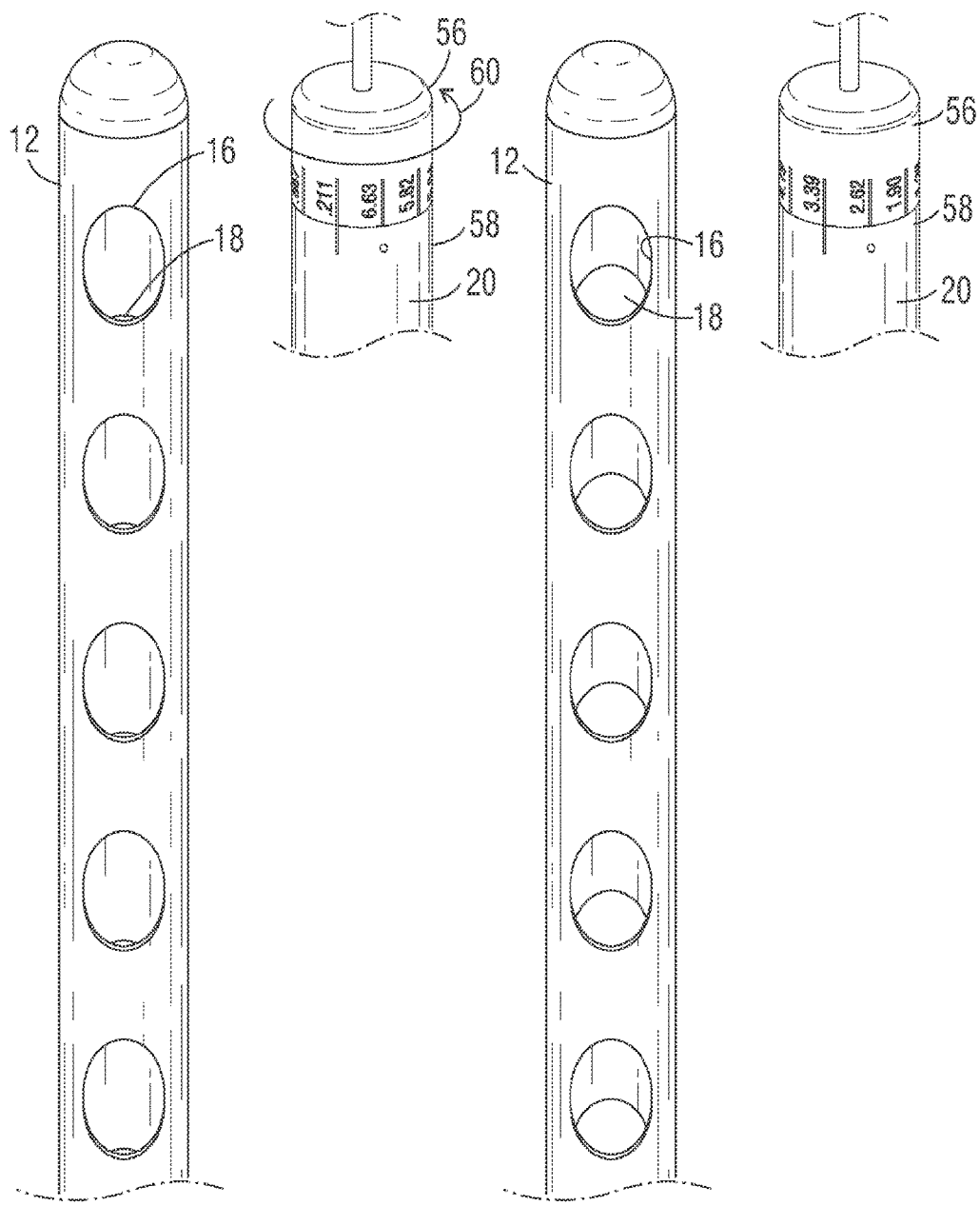

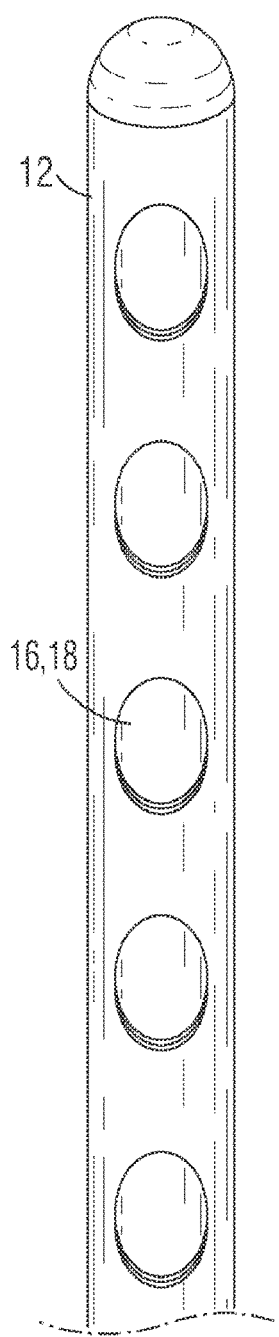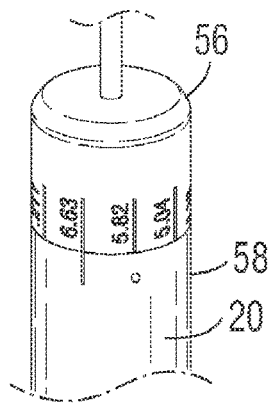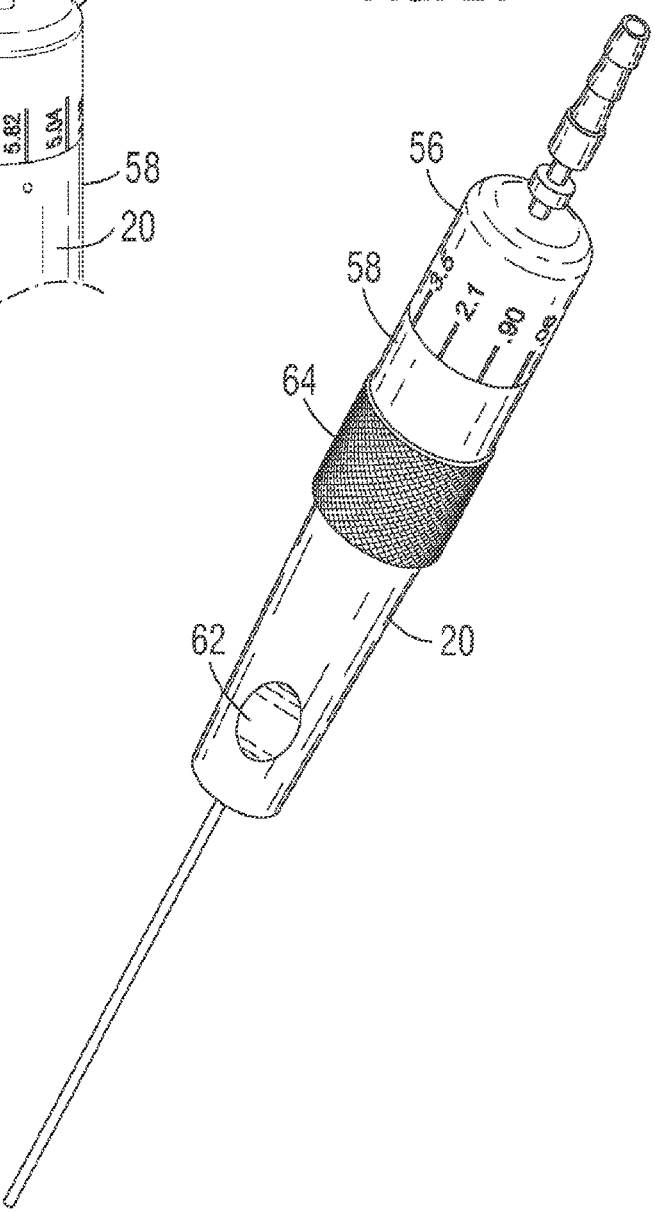

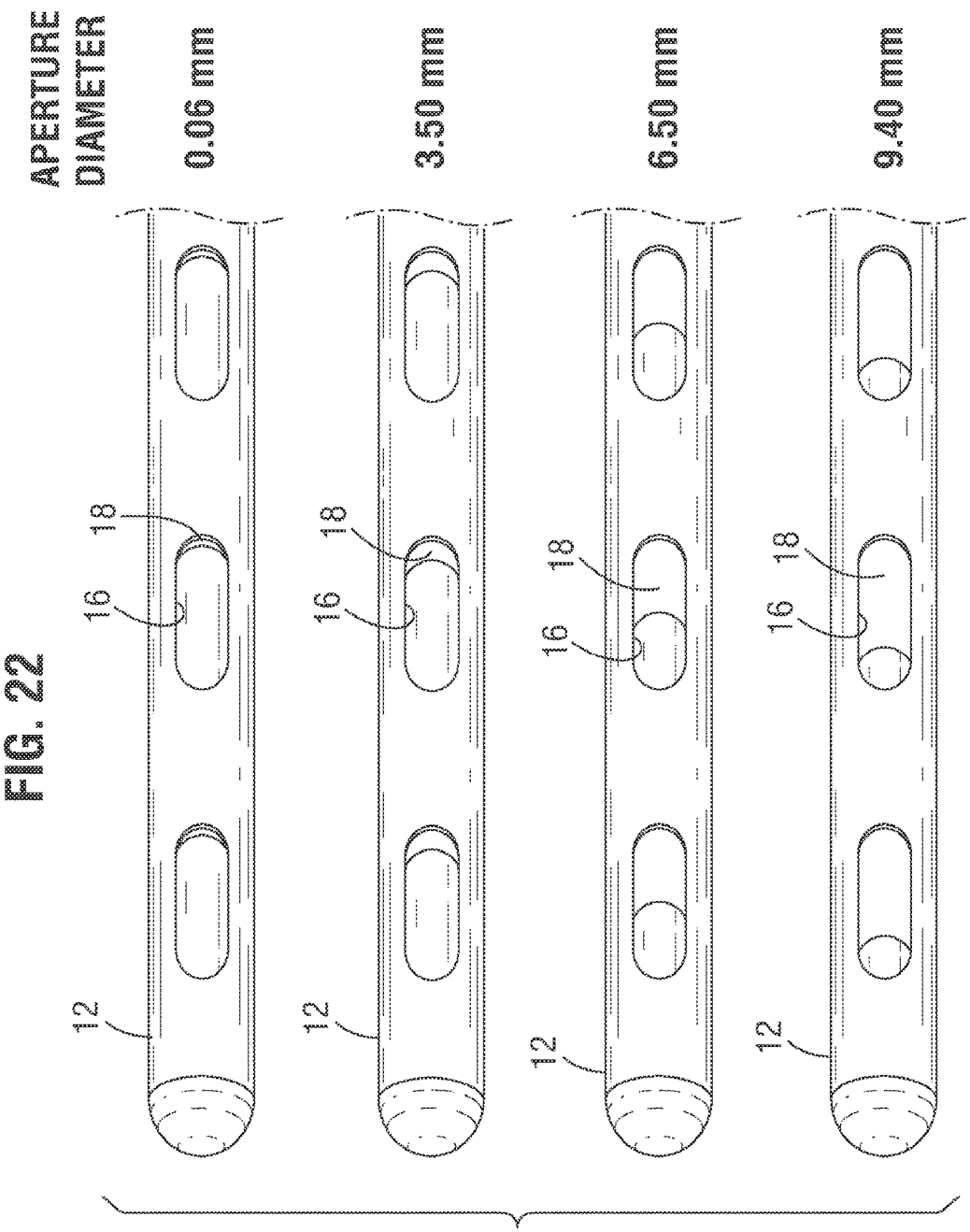

ADJUSTABLE LIPOSUCTION CANNULA

CROSS REFERENCE TO RELATED APPLICATIONS

This is the U.S. National Stage of International Application No. PCT/US2013/068762, filed Nov. 6, 2013, which was published in English under PCT Article 21(2), which in turn claims the benefit of U.S. Provisional Application No. 61/723,235, filed Nov. 6, 2012. The provisional application is incorporated by reference herein in its entirety.

FIELD

This disclosure relates to methods and systems for removing fat from the body.

BACKGROUND

Liposuction, or suction lipectomy, is a surgical procedure to remove fat from various locations in the body. Conventional liposuction procedures use cannulas coupled to suction devices to remove fat from the body. In this approach, the cannula is inserted into a region of fat and the suction device is activated to aspirate fat though openings in the cannula. The fat that is removed during this procedure can be disposed of or transferred to another location in the body, such as in breast reconstruction procedures or other fat transfer applications.

Conventional liposuction cannulas, however, have various drawbacks. For example, one drawback of conventional cannulas is that the sizes or types of openings in the cannula cannot be altered during a procedure. If the surgeon would like to change the size or type of openings in the cannula being used, he or she must remove the cannula from the patient and exchange it for a different cannula, which can increase the length of time that the patient is anesthetized. Additionally, a very large number of cannulas would be required to have a range of sizes and configurations of the openings in a liposuction cannula. Accordingly, there is a need for improved methods and systems for use during fat removal and/or fat transfer procedures.

SUMMARY

Various embodiments of adjustable cannula systems are disclosed herein. In one embodiment, an adjustable cannula system includes an outer hollow member and an inner hollow member. The outer hollow member has at least one outer opening through a wall of the outer hollow member. The inner hollow member has at least one inner opening through a wall of the inner hollow member. The inner hollow member is sized to be at least partly received within the outer hollow member. The inner hollow member is movable relative to the outer hollow member to adjust an amount of overlap between the at least one outer opening and the at least one inner opening, with the overlap of the outer opening(s) and the inner opening(s) defining one or more passageways on the adjustable cannula. In various embodiments, the outer opening(s) and/or the inner opening(s) can have a various shapes, such as rectangular, triangular (including three-sided openings with one or more contoured borders and/or one or more substantially straight borders), circular, elliptical, and/or bullet-shaped openings.

In some embodiments, the system further includes a handle and an adjustable member coupled to the handle. The adjustable member is moveable to cause the movement of the inner hollow member relative to the outer hollow member. The adjustable member can be movable between a plurality of discrete positions and an indicator can be provided that correlates the discrete positions with a predetermined size of the passageways formed in those respective discrete positions. In some embodiments, the handle can have numbering and/or other demarcations indicating the size of the passageways created.

In some embodiments, the adjustable member can include a rotatable member. The inner hollow member can be translatable along a longitudinal axis to adjust the amount of overlap and/or the inner hollow member can be rotatable about a longitudinal axis to adjust the amount of overlap. In other embodiments, the inner hollow member can be twistable about a longitudinal axis to adjust the amount of overlap. It should be understood that various combinations of translatable, rotatable, and deformable (e.g., twistable) inner and outer hollow members are possible.

The movement of the inner hollow member relative to the outer hollow member can change the number, size, and/or shapes of respective passageways. In some embodiments, the inner hollow member is movable between a first configuration in which passageways are on both a first side and a second side of the adjustable cannula, and a second configuration in which only passageways are provided on just one side.

In another embodiment, a method of removing fat from a patient is provided. The method can include inserting an adjustable cannula into a patient and changing the relative positions of an inner hollow member and an outer hollow member to alter an amount of overlap between openings in the outer hollow member and openings in the inner hollow member. The overlap of the first and second openings defining one or more passageways and a suction force can be applied to the adjustable cannula to aspirate fat from the patient through the passageways of the adjustable cannula.

In other embodiments, the act of changing the relative positions of the inner hollow member and the outer hollow member can include rotating an adjustable member coupled to a handle of the adjustable cannula. The rotation of the adjustable member can cause the inner hollow member to rotate, translate, and/or twist relative to the outer hollow member. In some embodiments, the size of the resulting passageways can be indicated based on the position of the adjustable member. In some embodiments, the surgeon can rotate a first portion (dial member) of the handle relative to a second portion (second member or second gripping member) of the handle to adjust the size of the passageways. In some embodiments, this adjustment includes aligning a passageway size indicator (such as a number and/or a corresponding mark) on either the first portion or the second portion, with a mark on the other portion.

The act of changing the relative positions of the inner hollow member and the outer hollow member can include changing the adjustable cannula from a first configuration in which the one or more passageways are located on more than one side of the adjustable cannula to a second configuration in which the one or more passageways are present on only one side of the adjustable cannula, with the first and second sides being spaced away from each other around the circumference of the outer hollow member.

In another embodiment, a device for attachment to a suction device for removing fat from a body includes a pair of nested hollow members that each has at least one opening and an adjustment means for adjusting the orientation of the nested hollow members from a first configuration to a second configuration. In the first configuration, there is a first amount of overlap between openings in the nested hollow members, and in the second configuration there is a second amount of overlap between openings in the nested hollow members, with the first and second amounts of overlap being different. In some embodiments, at least one of the nested members is deformable to change the shape of its respective openings.

The foregoing and other objects, features, and advantages of the invention will become more apparent from the following detailed description, which proceeds with reference to the accompanying figures.

BRIEF DESCRIPTION OF THE DRAWINGS

FIG. 1 illustrates an exemplary adjustable cannula system.

FIGS. 2A-2C illustrate exemplary components of an adjustable cannula system.

FIGS. 3A and 3B illustrate mechanisms for adjusting the passageways (e.g., overlapping openings of inner and outer hollow members) of an adjustable cannula system.

FIGS. 4A and 4B illustrate an exemplary manner in which the passageways of an adjustable cannula system can be altered.

FIG. 6 illustrate exemplary set of passageways of an adjustable cannula system.

FIG. 7 illustrate another exemplary set of passageways of an adjustable cannula system.

FIG. 8 illustrates another mechanism for adjusting the passageways of an adjustable cannula system.

FIG. 9 illustrates another view of the mechanism shown in FIG. 8.

FIG. 10 illustrates an exemplary pair of inner and outer hollow members for use in an adjustable cannula system.

FIG. 11A illustrates the exemplary pair of inner and outer hollow members of FIG. 10 in a first configuration.

FIG. 11B illustrates the exemplary pair of inner and outer hollow members of FIG. 10 in a second configuration.

FIG. 12 illustrates another exemplary pair of inner and outer hollow members for use in an adjustable cannula system.

FIG. 13A illustrates the exemplary pair of inner and outer hollow members of FIG. 12 in a first configuration.

FIG. 13B illustrates the exemplary pair of inner and outer hollow members of FIG. 12 in a second configuration.

FIG. 14 illustrates another exemplary pair of inner and outer hollow members for use in an adjustable cannula system.

FIG. 15A illustrates the exemplary pair of inner and outer hollow members of FIG. 14 in a first configuration.

FIG. 15B illustrates the exemplary pair of inner and outer hollow members of FIG. 14 in a second configuration.

FIG. 16 illustrates an exemplary pair of inner and outer hollow members that permit variation in the number and location of openings when combined.

FIGS. 17A and 17B illustrate the operation of the device illustrated in FIG. 16.

FIG. 18A illustrates another exemplary pair of inner and outer hollow members for use in an adjustable cannula system in a first configuration.

FIG. 18B illustrates a handle for use with the exemplary pair of inner and outer hollow members of FIG. 18A in the first configuration.

FIG. 19A illustrates the exemplary pair of inner and outer hollow members of FIG. 18A in a second configuration.

FIG. 19B illustrates the handle of FIG. 18B, as used with the exemplary pair of inner and outer hollow members of FIG. 19A in the second configuration.

FIG. 20A illustrates the exemplary pair of inner and outer hollow members of FIG. 18A in a third configuration.

FIG. 20B illustrates the handle of FIG. 18B, as used with the exemplary pair of inner and outer hollow members of FIG. 18A in the third configuration.

FIG. 21 illustrates another exemplary adjustable cannula system.

FIG. 22 illustrates another exemplary pair of inner and outer hollow members for use in the adjustable cannula system of FIG. 21, in various configurations.

DETAILED DESCRIPTION

Figure 3B:
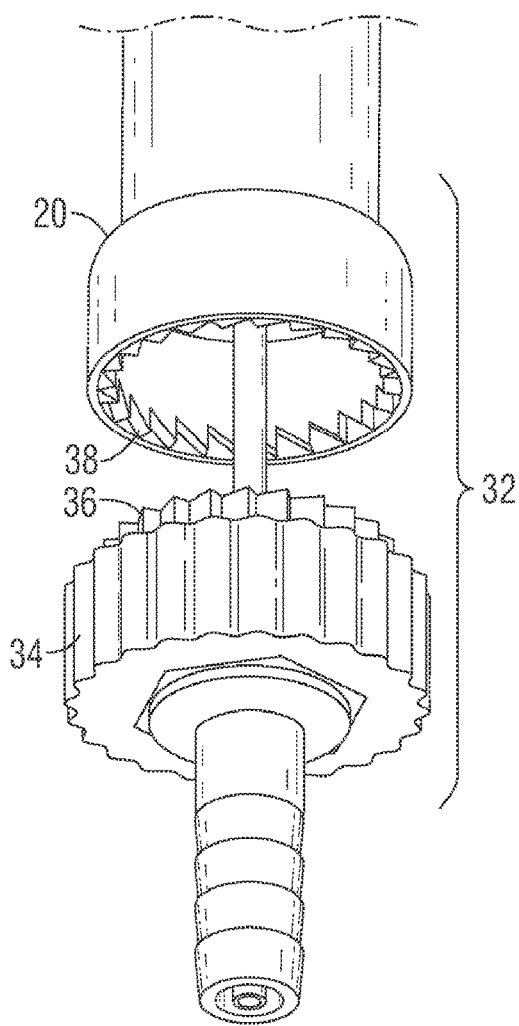

The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the terms "a," "an," and "the" include both the singular and plural forms of the element(s) they refer to unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language. The terms "fats" and "fatty tissue" are interchangeably used herein to refer to any fat-containing substance in the body that can be removed using the adjustable cannula systems disclosed herein.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Conventional cannulas have a single, non-adjustable opening configuration. In order to change the configuration, surgeons must exchange one cannula for another during a surgical procedure. The adjustable cannula systems described herein provide significant improvements over such conventional, non-adjustable cannulas. As described in more detail herein, the disclosed adjustable cannula systems allow a surgeon to adjust the size and/or number of openings in a cannula system without changing instruments. By reducing or eliminating the need to switch out cannulas during a procedure, the adjustable cannula system described herein can reduce surgery time, which in turn can reduce the amount of time that a patient is under anesthesia. In addition, the adjustability of the cannulas described herein not only allows surgeons to remove a greater variety of particle sizes and shapes, it can also allow them to more accurately target certain sizes of fatty tissue, which can be beneficial in both fat removal and fat transfer procedures. In some embodiments, the adjustable cannula system has low inter-cannula tolerances for minimal tissue damage during harvest.

FIG. 1 illustrates an adjustable cannula system 10. System 10 can be coupled to a suction device (not shown) via coupling member 11. The suction device can comprise any device capable of applying sufficient suction force to aspirate fat from the body.

System 10 can include a pair of nested hollow members 12, 14. Outer hollow member 12 can be sized to at least partly receive inner hollow member 14. As shown in more detail in FIGS. 2A-2C, outer hollow member 12 can comprise at least one opening 16 and inner hollow member 14 can comprise at least one opening 18. In the embodiment shown in FIGS. 1 and 2A-2C, outer hollow member 12 has a single rectangular opening 16 and inner hollow member 14 has a plurality of openings (e.g., six as shown in FIG. 2A). As shown in other embodiments, however, it should be understood that the number and size of openings 16 and 18 can vary.

To construct the system shown in FIG. 1, inner hollow member 14 can be positioned into a handle member 20. A biasing device 22 (e.g., a wave washer 24 and compression disc 26) can be placed over the outer shaft of inner hollow member 14 and the outer shaft and biasing device 22 can be positioned inside handle member 20. A clip or such other retaining member (not shown) can be positioned over a portion of the outer shaft (e.g., recessed slot 28) to secure inner hollow member 14 to handle member 20. Outer hollow member 12 can be positioned over inner hollow member 14 and a base portion 30 can be secured to handle member 20.

In operation, an adjustable member 32 (FIG. 3B) can be used to adjust the position of the opening(s) 18 of inner hollow member 14 relative the opening(s) 16 of outer hollow member 12. As shown in FIGS. 3A and 3B, the relative movement of openings 16, 18 can be achieved by rotating inner hollow member 14 relative to outer hollow member 12. For example, in one embodiment, adjustable member 32 can include a face gear system with a rotatable member 34 with a grooved surface 36 configured to engage with a facing grooved surface 38 inside of the handle member 20. Thus, as shown in FIG. 3A, a downward force in the direction of arrow 40 can be applied to rotatable member 34 to disengage the face gear system. Once the face gear system is disengaged, rotatable member 34 can be rotated (e.g., in the direction of arrow 42) to change the position of opening(s) 18 relative to opening(s) 16. Because the face gear system locks in discrete locations, movement of the adjustable member 32 (and therefore movement of inner hollow member 14 relative to outer hollow member 12) can be restricted to discrete positions. Since these discrete positions are known, indications can be provided (e.g., on the handle or elsewhere) that correlate an amount of rotation of the rotatable member with an amount of overlap between openings 16 and 18.

Although the relative movement illustrated in FIGS. 3A and 3B is rotation about a longitudinal axis of the system 10, and as discussed in other embodiments, herein, other relative movements that can change the relative positions of the openings 16, 18 are possible.

The overlap of opening(s) 16 and opening(s) 18 define one or more passageways through the system 10 and into a lumen 44 of inner hollow member 14. Thus, the defined passageways are the passageways through which fat or fatty tissue can be suctioned through the outer and inner hollow members 12, 14, into the lumen of inner hollow member 14, and out of the body.

The rotation of inner hollow member 14 can change the size and/or shape of its openings 18. For example, as shown in the exemplary embodiment of FIGS. 4A and 4B, the size and shape of the openings 18 can be adjusted by rotating inner hollow member 14 so that the openings 18 deform into a new shape. As shown in FIG. 4A, in a first configuration, openings 18 of inner hollow member 14 are generally rectangular in shape. However, as shown in FIG. 4B, in a second configuration, inner hollow member 14 is twisted so that the rectangular shapes of openings 18 deform to form a crescent shape. By twisting inner hollow member 14 so that it deforms (FIG. 4B), the size (i.e., the area) of the openings 18 that overlaps with opening 16 is decreased from the original configuration (FIG. 4A).

Figure 5A:
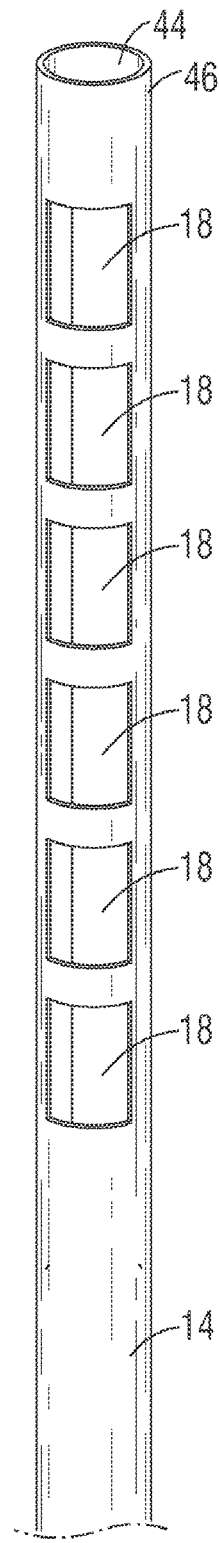
FIGS. 5A and 5B illustrate changes in size of openings in an inner hollow member of an adjustable cannula system.
Figure 5B:
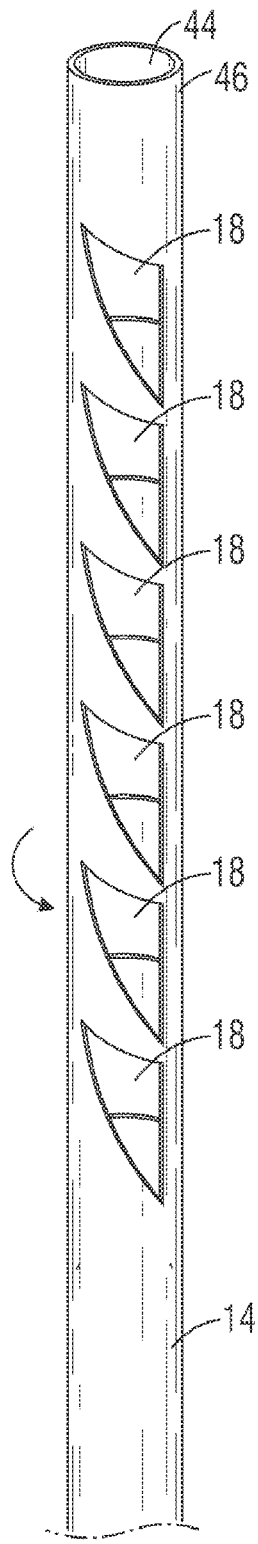

For further clarity, FIGS. 5A and 5B illustrate the deformation that occurs by rotating inner hollow member 14 in the manner discussed above. FIG. 5A illustrates inner hollow member 14 with generally rectangular-shaped openings 18, and FIG. 5B illustrates inner hollow member 14 after a force is applied in the direction of arrow 48 to alter the shape of openings 18. To facilitate the twisting deformation shown in FIG. 5B, a top portion 46 of inner hollow member 14 can be fixed relative to outer hollow member 12.

Accordingly, in this embodiment, openings 16 of outer hollow member 12 are fixed in size and the movement (e.g., twisting) of inner hollow member 14 causes a change in the size and shape of the passageways formed between outer and inner hollow members 12, 14.

FIGS. 6 and 7 illustrate other exemplary shapes and sizes of openings 18. For example, FIG. 6 illustrates triangular-shaped openings 18, while FIG. 7 illustrates teardrop-shaped openings 18. In addition, instead of a single opening in the outer hollow member 12 (as shown in FIG. 2B), FIGS. 6 and 7 illustrate outer hollow members 12 that have a plurality of openings 16 that can overlap with openings 18 in inner hollow members 14 to form fat-receiving passageways.

FIGS. 8 and 9 illustrate another mechanism by which the relative positions of openings 16 and 18 can be varied. For example, instead of a face gear system, adjustable member 32 can comprise a spring-loaded ball and detent system. In this embodiment, metal balls sliding within a bored cylinder can engage with a recessed member (e.g., a detent) to restrict movement of the adjustable member 32 to discrete positions.

Other adjustable members and configurations of inner and outer hollow members are possible. For example, FIGS. 10, 11A, and 11B illustrate an embodiment where the adjustable member is moved along a longitudinal axis of the system (e.g., distally or proximally) to adjust the shapes and/or sizes of the passageway(s). FIG. 10 illustrates an outer hollow member 12 and an inner hollow member 14 with openings of the same general size and shape. However, as shown in FIGS. 11A and 11B, movement of inner hollow member 14 in the direction of arrow 50 can cause the size and shape of the overlap between openings 16 and 18 to change. For example, in FIG. 11A, the passageways (e.g., the overlap between openings 16 and 18) are large and generally rectangular, while in FIG. 11B, after moving inner hollow member 14 relative to outer hollow member 12, the passageways are smaller and generally square.

Longitudinal movement of the inner hollow member relative to the outer hollow member can be achieved in various manners. For example, a drive system can be provided with a rotatable gear that has a surface that engages with an outer surface of the inner hollow member so that rotation of the drive system will cause the inner hollow member to translate longitudinally relative to the outer hollow member.

FIGS. 12, 13A, and 13B illustrate another embodiment of an adjustable cannula system. In this embodiment, various size openings are disclosed on the same system. Thus, for example, there are larger openings and smaller openings on both the outer and inner hollow members 12, 14. Relative movement of the outer and inner hollow members 12, 14 (e.g., longitudinal movement in the direction of arrow 52) can cause the area of the passageways to decrease as shown in FIGS. 13A and 13B.

FIGS. 14, 15A, and 15B illustrate another embodiment of an adjustable cannula system. In this embodiment, not only do the sizes of the openings vary, but the shapes of the openings also vary. Thus, for example, there are larger rectangular openings and smaller circular openings on both the outer and inner hollow members 12, 14. Relative movement of the outer and inner hollow members 12, 14 (e.g., longitudinal movement in the direction of arrow 54) causes the area of the passageways to decrease as shown in FIGS. 13A and 13B.

FIGS. 16, 17A, and 17B illustrate another embodiment of an adjustable cannula system. In this embodiment, passageways on different sides of the cannula system can be selectively opened and/or closed. For example, outer hollow member 12 can have two or more sets of openings radially spaced apart along the circumference of outer hollow member 12. As shown in FIG. 17A, inner hollow member 14 can be sized so that it can be moved relative to outer hollow member 12 into a first configuration where openings 18 on inner hollow member 14 overlap with the two (or more) sets of openings 16 on outer hollow member 12 to form passageways at the two (or more) sets of openings. As shown in FIG. 17B, relative movement of inner hollow member 14 into a second configuration closes at least some of the sets of the openings in outer hollow member 12, so that passageways are formed using less than all of the sets of openings 16 in outer hollow member 12. In this manner, the surgeon can not only selectively change the size and/or number of passageways, the surgeon can alter the location of these openings so that they are all one side, or spread out around the circumference of the cannula system.

FIGS. 18A-21 illustrate an additional embodiment of an adjustable cannula system. In this embodiment, the handle 20 comprises a dial member 56 which can be rotated relative to a second member 58, to manually select between settings corresponding to passageway diameters. For example, a surgeon can rotate the dial member 56 in FIG. 18B, as indicated by arrow 60, to change the passageway size setting from 0.211 mm (FIG. 18B) to 3.39 mm (FIG. 19B) or 6.63 mm (FIG. 20B). This rotation of the handle 20 can cause the inner hollow member 14 to translate relative (e.g., by the telescoping action provided in the longitudinal direction) to the outer hollow member 16, thus effecting an increase in the size of the passageways (FIG. 19A) in accordance with the new setting. As shown in FIGS. 18B, 19B and 20B, a line or another mark on the second member 58 can be aligned with a number (or a line or other demarcation associated with the number) on the dial member 56 corresponding to the desired passageway size. In another embodiment, the placements are reversed such that the numbering appears on the second member 58.

As shown in FIGS. 18A, 19A and 20A, the outer hollow members 12 can have a plurality of elliptical openings 16 that can overlap with elliptical openings 18 in the inner hollow member 14 to form fat-receiving passageways. In another embodiment, the outer hollow member 12 can have a plurality of circular openings 16 that can overlap with circular openings 18 in the inner hollow member 14 to form fat-receiving passageways.

FIGS. 21-22 illustrate an additional embodiment of an adjustable cannula system, which also has a dial member 56.

As shown in FIG. 21, the handle 20 can comprise a gripping second member 58 with ergonomic surface features to improve manual control, including an indentation 62 (such as for secure placement of a thumb) and a gripping surface 64. The gripping surface 64 can include raised surface features and/or grating. FIG. 22 illustrates various different configurations of the outer hollow member 12 and the inner hollow member 14, matched to the passageway (i.e., aperture) diameters created. In this embodiment, the outer hollow member 12 can have a plurality of bullet shaped openings 16 (rounded at one or both ends with a straight elongated section in between) that can overlap with bullet shaped openings 18 in the inner hollow member 14 to form fat-receiving passageways. In various configurations, the cannula system of FIG. 22 can have various other passageway sizes between about 0.1 mm and about 12.4 mm. In other embodiments, larger passageway sizes are possible, such as about 13 mm, about 14 mm and/or about 15 mm. The adjustable cannula system of FIG. 21 is not limited to any particular shape, size or number of passageways.

In various embodiments, the outer hollow member 12 and/or the inner hollow member 14 can have several openings. For example, in various embodiments, the outer hollow member 12 and/or the inner hollow member 14 can each have numerous openings 16, 18, such as four, five, six, seven, eight, nine or ten openings. Thus, in various embodiments, several passageways can be created, such as four, five, six, seven, eight, nine or ten passageways.

The embodiments disclosed herein provide for changing the effective working size of openings by moving an inner hollow member relative to an outer hollow member. To achieve this relative movement, either one of the hollow member, or both, can be moved. For example, to adjust the size of openings, (1) the inner hollow member can be moved (e.g., longitudinally or rotationally) while the outer hollow member is maintained in position, (2) outer hollow member can be moved (e.g., longitudinally or rotationally) while the inner hollow member is maintained in position, or (3) both the inner and outer hollow members can be moved at the same time.

The systems disclosed herein can be used in various combinations. Thus, for example, an outer hollow member disclosed in FIG. 12 can be used in with an inner hollow member disclosed in FIG. 10. Additionally, it should be understood that the size, shape and/or function of the openings in the various inner and outer hollow members can be switched and/or combined. For example a fixed outer opening can be replaced with a deformable outer opening, resulting in a device that allows the outer hollow member to rotate to deform the size/shape of the openings on the outer hollow member. In the same device, the inner opening can remain a deformable opening or, alternatively, the inner opening can be switched with a fixed size opening that does not deform.

When the functions of the inner and outer hollow members are switched, the system operates in the same general manner except that the functions of the openings would be reversed. For example, the openings of the inner and outer hollow members of FIGS. 4A and 4B can be reversed so that the fixed openings of outer hollow member are replaced with deformable openings and the deformable openings of the inner hollow member are replaced with fixed openings. Thus, to vary the size of the deformable openings, the outer hollow member would be twisted instead of the inner hollow member.

The handle and lumen members can be detachable relative to one another to permit a surgeon to change instruments before or during a surgical procedure. In addition, if desired, alternative size handles can be provided to allow the surgeon to select a handle size that he or she finds most comfortable.

As discussed above, the cannulas described herein can be used in connection with liposuction procedures, fat transfer procedures, or any other procedure that involves aspiration of tissues or fluid from the body. In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An adjustable cannula, comprising;
   an outer hollow member having a plurality of outer openings through a wall of the outer hollow member; and
   an inner hollow member having a plurality of inner openings through a wall of the inner hollow member, the inner hollow member being sized to be at least partly received within the outer hollow member;
   wherein respective ones of the plurality of inner openings or respective ones of the plurality of outer openings are adjustable from a first shape to a second shape that is different from the first shape, and
   wherein the inner hollow member is movable relative to the outer hollow member to adjust an amount of overlap between the plurality of outer openings and the plurality of inner openings, the overlap of respective outer openings with respective inner openings defining a plurality of passageways on the adjustable cannula through the outer hollow member and inner hollow member.

2. The adjustable cannula of claim 1, further comprising:
   a handle; and
   an adjustable member coupled to the handle, the adjustable member being moveable to cause the movement of the inner hollow member relative to the outer hollow member.

3. The adjustable cannula of claim 2, wherein the adjustable member is movable between a plurality of discrete positions.

4. The adjustable cannula of claim 3, further comprising an indicator that correlates the plurality of discrete positions with a predetermined size of the passageways formed in respective discrete positions.

5. The adjustable cannula of claim 3, wherein the adjustable member comprises a rotatable member.

6. The adjustable cannula of claim 1, wherein the inner hollow member is translatable along a longitudinal axis to adjust the amount of overlap between respective outer openings and respective inner openings.

7. The adjustable cannula of claim 1, wherein the inner hollow member is rotatable about a longitudinal axis to adjust the amount of overlap between respective outer openings and respective inner openings.

8. The adjustable cannula of claim 1, wherein the inner openings are adjusted from the respective first shapes to the respective second shapes when the inner hollow member is twisted about a longitudinal axis to adjust the amount of overlap between respective outer openings and respective inner openings.

9. The adjustable cannula of claim 1, wherein the movement of the inner hollow member relative to the outer hollow member changes the sizes of respective ones of the plurality of passageways.

10. The adjustable cannula of claim 1, wherein the movement of the inner hollow member relative to the outer hollow member changes the number of respective ones of the plurality of passageways.

11. The adjustable cannula of claim 1, wherein the inner hollow member is movable between a first configuration that includes passageways on both a first side and a second side of the adjustable cannula, and a second configuration in which only passageways on one of the first or second sides of the adjustable cannula are provided, the first and second sides being spaced away from each other around the circumference of the outer hollow member.

12. The adjustable cannula of claim 1, wherein the first shape is a rectangular shape and the second shape forms, at least in part, a crescent shape.

13. The adjustable cannula of claim 1, wherein a top portion of the inner hollow member is fixed to the outer hollow member and the plurality of outer openings are fixed in size and shape.

14. A method of removing fat from a patient, comprising:
    inserting an adjustable cannula into a patient, the adjustable cannula comprising an inner hollow member disposed at least partly within an outer hollow member;
    changing the relative positions of the inner hollow member and the outer hollow member to alter an amount of overlap between a plurality of first openings through a wall of the outer hollow member and a plurality of second openings through a wall of the inner hollow member, the overlap of respective first openings and respective second openings defining one or more passageways;
    adjusting a geometric shape of respective ones of the plurality of inner openings or respective ones of the plurality of outer openings, the geometric shape changing of the respective ones of the inner or outer openings changing from a first shape to a second shape that is different from the first shape; and
    applying a suction force to the adjustable cannula to aspirate fat from the patient through the passageways of the adjustable cannula.

15. The method of claim 14, wherein the act of changing the relative positions of the inner hollow member and the outer hollow member comprises:
    rotating an adjustable member coupled to a handle of the adjustable cannula.

16. The method of claim 15, wherein the rotation of the adjustable member cause the inner hollow member to rotate relative to the outer hollow member.

17. The method of claim 15, wherein the rotation of the adjustable member causes the inner hollow member to twist, the twisting of the inner hollow member causing the respective second openings to change from the first shape to the second shape.

18. The method of claim 15, wherein the rotation of the adjustable member causes the outer hollow member to twist, the twisting of the outer hollow member causing the respective first openings to change from the first shape to the second shape.

19. The method of claim 15, wherein the rotation of the adjustable member cause the inner hollow member to translate longitudinally relative to the outer hollow member.

20. The method of claim 15, further comprising indicating a size of the one or more passageways based on a position of the adjustable member.

21. The method of claim 14, wherein the act of changing the relative positions of the inner hollow member and the outer hollow member comprises:

changing the adjustable cannula from a first configuration in which the one or more passageways are located on more than one side of the adjustable cannula to a second configuration in which the one or more passageways are present on only one side of the adjustable cannula, the first and second sides being spaced away from each other around the circumference of the outer hollow member.

* * * * *